United States Patent [19]

Jagdmann et al.

[11] Patent Number: 5,273,972
[45] Date of Patent: Dec. 28, 1993

[54] [(2-DIAKYLAMINOMETHYL)-3-QUINU-CLIDINYL]-BENZAMIDES AND BENZOATES

[75] Inventors: Gunnar E. Jagdmann, Apex, N.C.; Harry R. Munson, Jr., Leawood, Kans.

[73] Assignee: A. H. Robins Company, Incorporated, Richmond, Va.

[21] Appl. No.: 858,257

[22] Filed: Mar. 26, 1992

[51] Int. Cl.$^5$ .................. A61K 31/46; C07D 453/02
[52] U.S. Cl. .................. 514/210; 514/233.5; 514/305; 544/127; 546/133; 546/137
[58] Field of Search .............. 544/127; 546/133, 137; 514/305, 233.5, 210

[56] References Cited

U.S. PATENT DOCUMENTS

| | | | |
|---|---|---|---|
| 3,598,825 | 8/1971 | Biel | 260/268 |
| 3,726,877 | 4/1973 | Elkin | 544/127 X |
| 4,593,034 | 6/1986 | Munson | 514/305 |
| 4,657,911 | 4/1987 | Imbert | 514/272 |
| 4,826,838 | 5/1989 | Richardson | 514/210 |
| 4,908,370 | 3/1990 | Naylor | 514/305 |
| 5,017,580 | 5/1991 | Naylor | 514/299 |

FOREIGN PATENT DOCUMENTS

| | | |
|---|---|---|
| 0202062 | 5/1986 | European Pat. Off. . |
| 450757 | 10/1991 | European Pat. Off. . |
| 2625678 | 1/1988 | France . |

OTHER PUBLICATIONS

Chemical Abstracts Service CA 116: 91380 b 1991 (Corresp. to EP 450757).
Mikhlina et al. Khim. Farmatsevt Zh. 7, No. 8, 20-24 (1973),.
Barnes et al., J. Pharm. Pharmacol. 198, 40:668. (1988).
Kilpatrick. Nature, 330, 24/31, 746-748 (1987).
Costal et al., Pharm. Ther. 47, 181-202 (1990).
Kidd et al., Eur. J. Pharmacol. 211, 133-136 (1992).
Wise and Heffner, "Antipsychotics," Ann. Repts. Med. Chem., 26, 53-62, 1991.
Audia and Cohen, "Serotonin Modulators and Cardiovascular/Gastrointestinal Diseases," Ann. Repts. Med. Chem. 26, 103-112, 1991.
Robertson and Fuller, "Central Serotonin Receptors," Ann. Rpts. Med. Chem. 23, 49-58, 1988.
Johnson, "Recent Advances in Migraine Research," Ann. Rpts. Med. Chem. 22, 41-50, 1987.

*Primary Examiner*—Howard T. Mars
*Assistant Examiner*—Catherine Scalzo
*Attorney, Agent, or Firm*—R. F. Boswell, Jr.

[57] ABSTRACT

This invention provides novel 2-substituted-3-quinuclidinyl arylcarboxamides and arylthiocarboxamides and corresponding arylcarboxylates which have utility as therapeutic agents which exhibit gastric prokinetic, antiemetic, anxiolytic and 5-HT (serotonin) antagonist effects in warm blooded animals.

Illustrative of an invention compound is 5-chloro-2-methoxy-4-(methylamino)-N-[2-(1-piperidinylmethyl)-1-azabicyclo[2.2.2]oct-3-yl]benzamide:

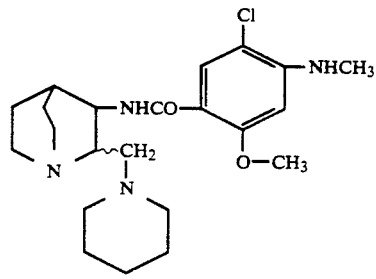

or a pharmaceutically acceptable salt thereof.

18 Claims, No Drawings

[(2-DIAKYLAMINOMETHYL)-3-QUINU-CLIDINYL]-BENZAMIDES AND BENZOATES

BACKGROUND OF THE INVENTION

Quinuclidine analogs of sulpiride were prepared and studied by Mikhlina, E. E. et al as reported in Khim-Farmastsevt. Zh. 10, No. 11, 56–60 (1976); C.A. 86: 155489r exemplified by the compound: 5-aminosulfonyl-N-(1-azabicyclo-[2.2.2]oct-3-yl)-2-methoxybenzamide. This compound and others in the series were reported by the authors not to have anti-emetic activity. The above named compound was reported in USSR Pat. No. SU-414-261 to have neuroleptic activity. The compounds of the present invention show anti-emetic activity without the neuroleptic activity associated with dopamine $D_2$-receptor blockade (blockade of d-amphetamine lethality in mice).

Syntheses of 4-amino-N-(1-azabicyclo[2.2.2]oct-3-yl)benzamide and N-(1-azabicyclo[2.2.2]oct-3-yl)benzamide were reported by Mikhlina, E. E. et al in Khim-Farmatsevt. Zh. 7, 20–24 (1974); C.A. 79: 146358a and the latter in Khim. Geterosikl. Soedin., Akad. Nauk. Latv. SSR 243–9 (1966); C.A. 65: 2220b. The compounds were reported to exhibit hypotensive, narcotic and ganglionic stimulation and blocking activities, properties not seen in the compounds of the present invention.

Synthesis of 4-amino-N-(1-azabicyclo[2.2.2]oct-3-yl)-3-chloro-5-trifluoromethylbenzamide was reported in Ger. Offen. No. 2,548,968; C.A. 87: 68001c and equivalently related U.S. Pat. No. 4,093,734 from 4-amino-3-chloro-5-trifluoromethylbenzoic acid chloride and 3-aminoquinculidine. The compound is in a class among pyrrolidinyl and piperidinyl benzamides which are said to be useful as anxiolytics, anticonvulsives, antiemetics and antiulcerogenics.

G.B. 2,160,871A describes ether and thioether benzamide derivatives of dialkylaminoalkylamine or 1-alkyl-4-aminopiperidines that are useful in the treatment of emesis, and also the treatment of impaired gastric motility disorders. The patent compounds are analogs of metoclopramide and clebropride.

U.S. Pat. Nos. 4,593,034; 4,657,911; and 4,717,563 describe benzoyl derivatives of 1-azabicyclo[2.2.2]octan-3-amine (3-aminoquinuclidine) and 1-azabicyclo[2.2.2]octan-3-ol (3-quinuclidinol) which exhibit gastric prokinetic and antiemetic effects in warm blooded animals.

U.S. Pat. No. 4,722,834 describes 2-alkoxy-N-(1-azabicyclo[2.2.2]oct-3-yl)benzamide-N-oxides which are useful for the control of emesis caused by administration of anticancer drugs to warm blooded animals.

There is continuing interest in the development of quinuclidine derivatives which exhibit a novel combination of therapeutic properties for the treatment of disorders in warm blooded animals, with minimal neuropharmacological side effects.

Accordingly, it is an object of this invention to provide a novel class of N-[(2-dialkylaminomethyl)-3-quinuclidinyl]benzamides and thiobenzamides, and corresponding carboxylates.

It is another object of this invention to provide quinuclidine derivatives which exhibit gastric prokinetic, antiemetic, anxiolytic and selective 5-HT(serotonin) antagonist effects in warm blooded animals.

It is a further object of this invention to provide a method for the treatment of impaired gastrointestinal motility and/or emesis and/or anxiety in warm blooded animals.

Other objects and advantages of the present invention shall become apparent from the accompanying description and examples.

DESCRIPTION OF THE INVENTION

One or more objects of the present invention are accomplished by the provision of 3-quinuclidinyl benzamide and benzoate derivatives corresponding to the formula:

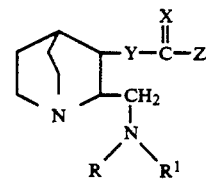

where X is oxygen or sulfur; Y is —NH— or —O—; R and $R^1$ are $C_1$–$C_4$ alkyl, or R and $R^1$ taken together with the connecting nitrogen atom is a 4–6 membered heterocyclic structure selected from azetidine, pyrrolidine, piperidine or morpholine;

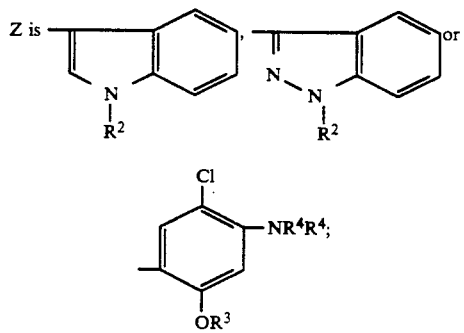

$R^2$ is hydrogen or a $C_1$–$C_4$ alkyl substituent; $R^3$ is a hydrogen, $C_1$–$C_4$ alkyl, $C_1$–$C_4$ alkenyl, $C_2$–$C_6$ alkylthioalkyl or $C_2$–$C_6$ substituent; and $R^4$ is hydrogen or a $C_1$–$C_4$ alkyl substituent; and geometrical and optical isomers, and pharmaceutically acceptable salts thereof.

Illustrative of $C_1$–$C_4$ alkyl, $C_1$–$C_4$ alkenyl, $C_2$–$C_6$ alkylthioalkyl or $C_2$–$C_6$ alkyloxyalkyl substituents are methyl, ethyl, propyl, 2-propyl, allyl, butyl, 2-butyl, isobutyl, methylthiomethyl, methylthioethyl, methylthiopropyl, ethylthioethyl, methyloxymethyl, methyloxyethyl, methyloxypropyl, ethyloxyethyl, and the like.

The invention compounds in the form of geometrical and optical isomeric mixtures can be isolated as pure isomer fractions by conventional preparation procedures.

The term "pharmaceutically acceptable acid addition salts" as employed herein refers to the acid addition salts, hydrates, alcoholates and salts of the compounds represented by Formula I which are physiologically compatible in warm blooded animals. The acid addition salts are formed with inorganic and organic acids such as hydrochloric, sulfuric, phosphoric, fumaric, maleic, succinic, citric, tartaric, cyclohexamic, and the like.

In another embodiment this invention provides a method for the treatment of warm blooded animals for emesis caused by administration of anticancer drugs such as cisplatin during cancer treatment which comprises internally administering to said animals an emesis-inhibiting effective amount of a quinuclidine derivative corresponding to Formula I as represented above. An invention quinculidine derivative also is applicable for the treatment of emesis caused by administration of non-platinum anticancer drugs such as mechlorethamine hydrochloride, doxorubicin, dactinomycin and dacarbazine.

In another embodiment this invention provides a method for the treatment of warm blooded animals for impaired gastrointestinal motility which comprises internally administering to said animals a gastric motility-enhancing effective amount of a quinuclidine derivative corresponding to Formula I as represented above.

In a further embodiment this invention provides a method for the treatment of warm blooded animals for anxiety symptoms which comprises internally administering to said animals an anxiety-alleviating effective amount of a quinuclidine derivative corresponding to Formula I as represented above.

The quinuclidine derivatives of the present invention also can be effective in treatment of disorders associated with an imbalance of 5-HT(serotonin), by inhibition or modulation of selective 5-HT activities, and thus can be useful in the treatment of migraine headaches, psychoses, and disorders of memory and learning.

A present invention Formula I compound is administered to warm blooded animals in a wide variety of conventional pharmaceutical dosage forms, preferably in combination with a non-toxic pharmaceutical carrier. The active agent is administered orally, subcutaneously, intravenously or intramuscularly and, if necessary, in repeated doses until satisfactory response is obtained. The daily dosage is from about 0.1 to about 300 mg of active medication, advantageously from about 0.1 mg to 50 mg.

Compositions for oral administration can be in the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid, e.g., water or arachis oil contained in ampoules.

The pharmaceutical compositions for use in conjunction with administration of anticancer drugs in cancer treatment will be formulated to contain from about 0.1 mg/kg to about 50 mg/kg body weight, preferably 1.0 mg/kg body weight or less of a compound of Formula I.

In all of the above, it is only necessary that a suitable effective dosage is consistent with the dosage form employed. The exact individual dosages, as well as daily dosages, will be determined according to standard medical principles under the direction of a physician or veterinarian.

Preparation Of Invention Compounds

A quinuclidinyl benzamide of the present invention can be prepared by (a) reacting a 3-quinuclidinone under Mannich reaction conditions to provide a 2-(disubstitutedaminomethyl)-3-quinuclidinone, followed by conversion to the oxime; (b) reduction of the oxime to provide a 2-(disubstitutedaminomethyl)-3-aminoquinuclidine; (c) coupling of the 3-aminoquinuclidine with an arylcarboxylic acid to yield an invention benzamide; and (d) optional conversion of the benzamide to the corresponding thiobenzamide.

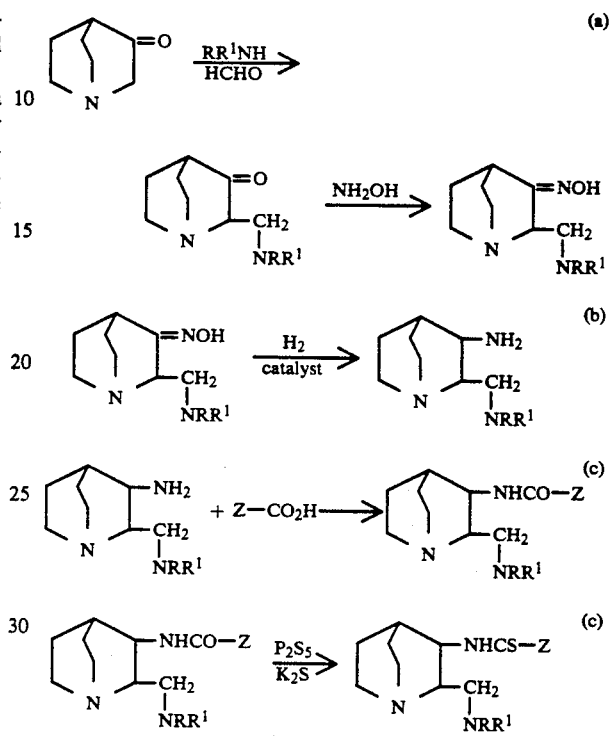

A quinuclidinyl arylcarboxylate of the present invention Formula I can be prepared by (a) reducing 3-(2-disubstitutedaminomethyl)quinuclidinone to provide 3-(2-disubstitutedaminomethyl)quinuclidinol; and (b) reacting the quinuclidinol derivative with an arylcarboxylic acid to yield a Formula I quinuclidinyl arylcarboxylate; and (c) optional conversion of the carboxylate ester to the corresponding thiocarboxylate ester.

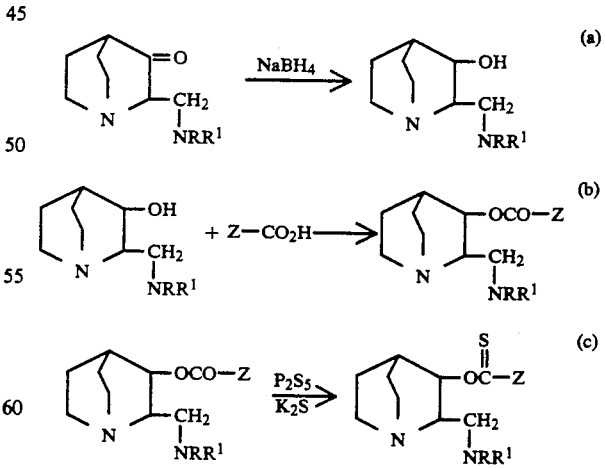

The following examples are further illustrative of the present invention. The components and specific ingredients are presented as being typical, and various modifications can be derived in view of the foregoing disclosure within the scope of the invention.

Intermediate 1

4-Amino-5-chloro-2-[2-(methylthio)ethoxy]benzoic acid

A. 4-Amino-5-chloro-2-hydroxybenzoic acid

A cooled (5° C.) suspension of 60% sodium hydride oil dispersion (20.0 g, 0.50 mole) in anhydrous dimethylformamide (300 ml) under nitrogen was treated dropwise with ethyl mercaptan (18.7 g, 0.3 mole) while maintaining the reaction temperature below 15° C. The solution was stirred for 15 minutes at 25° C., cooled (5° C.), and treated in small portions with 4-amino-5-chloro-2-methoxybenzoic acid (40.33 g, 0.2 mole). The mixture was heated to 105°±5° C. for 4 hours, cooled, concentrated in vacuo to remove most of the dimethylformamide, then diluted with water (500 ml). The aqueous solution was extracted with methylene chloride (2×150 ml), then with ether (150 ml), acidified with concentrated HCl (55 ml), filtered, and the filter cake was washed with water and dried in vacuo in the presence of Drierite to provide a crude product. The product was recrystallized from tetrahydrofuran/hexane to yield 31.3 g (83%) of white solid, mp 192° C.

B. 4-Amino-5-chloro-2-[(2-methylthio)ethoxy]benzoic acid

A cooled (5° C.) suspension of 60% sodium hydride oil dispersion (0.52 g, 13 mmole) in anhydrous dimethylformamide (15 ml) under nitrogen was treated in portions with 4-amino-5-chloro-2-hydroxybenzoic acid (0.94 g, 5 mmoles) stirred for 15 minutes at 25° C., treated with (2-chloroethyl)methyl sulfide (1.66 g, 15 mmoles), and heated to 100°±5° for 18 hours. The solution was cooled, concentrated in vacuo to remove most of the dimethylformamide, and water (25 ml) was added. The aqueous solution was extracted with ether (2×25 ml), and the combined extracts were dried (MgSO$_4$), concentrated in vacuo, taken up in 50% aqueous ethanol (50 ml), treated with potassium hydroxide (5.0 g), and refluxed for one hour. The mixture was concentrated to remove most of the ethanol, diluted with water to 75 ml total volume, extracted with ether (2×35 ml), and acidified to pH 3 with concentrated HCl. The resultant precipitate was filtered, washed with water, air dried, and recrystallized from ethyl acetate to yield 0.74 g (57%) of fine voluminous white needles, mp 137.5°-139.5° C.

Anal. Calc. for C$_{10}$H$_{12}$ClNO$_3$S: C,45.89; H,4.62; N,5.35. Found: C,45.96; H,4.72; N,5.32.

Intermediate 2

2-(1-Piperidinylmethyl)-1-azabicyclo[2.2.2]octan-3-one oxime

A slurry of 3-quinuclidinone hydrochloride (16.2 g, 100 mmoles) in ethanol (16.5 ml) and water (7 ml) was treated with sodium hydroxide (4.0 g, 100 mmoles) and stirred for 15 minutes. Separately, a cooled (0° C.) mixture of piperidine (15 ml, 150 mmoles), water (15 ml), and ethanol (10 ml) was treated with 37% aqueous formaldehyde (11.5 ml, 150 mmoles), and the mixture was stirred at room temperature for 15 minutes. The mixtures were combined, refluxed for 45 minutes, cooled, and diluted with petroleum ether (250 ml). The organic layer was separated and the aqueous solution was extracted with petroleum ether (100 ml). The combined organic layers were dried (MgSO$_4$), concentrated in vacuo, and dissolved in methanol (100 ml). Hydroxylamine hydrochloride (7.7 g, 110 mmoles) was added, followed by 25% sodium methoxide/methanol (2.16 g, 10 mmoles), and the mixture was stirred for 18 hours. Additional 25% sodium methoxide (21.6 g, 100 mmoles) was added, and the methanol was removed in vacuo and replaced with water (100 ml). The suspension was filtered, and the solid was collected and dried. The filtrate was saturated with sodium chloride, extracted with methylene chloride (3×100 ml), and the combined extracts were dried (Na$_2$SO$_4$), concentrated in vacuo, and triturated from ether. The combined solids were recrystallized from 2-propanol to yield 4.1 g (17%) of voluminous white needles, mp 196°-198° C. (dec).

Anal. Calc. for C$_{13}$H$_{23}$N$_3$O: C,65.79; H,9.77; N,17.70. Found: C,65.95; H,9.95; N,17.73.

Intermediate 3

2-(1-Pyrrolidinylmethyl)-1-azabicyclo[2.2.2]octan-3-one oxime

A suspension of quinuclidine-3-one hydrochloride (16.2 g, 0.1 mole) in 95% ethanol (25 ml) was treated with 50% sodium hydroxide (8.0 g, 0.1 mole) and stirred until homogeneous. In a separate reactor a cooled (0° C.) solution of pyrrolidine (10.7 g, 0.15 mole) in 95% ethanol (25 ml) was treated dropwise with 37% aqueous formaldehyde (11.5 ml, 0.15 mole), and the solution was stirred at 25° C. for 30 minutes. The two solutions were combined and the mixture was refluxed for 4 hours, cooled, and added to ether (250 ml). Magnesium sulfate was added, and the mixture was stirred for 15 minutes and filtered. The filtrate was concentrated in vacuo, dissolved in methanol (100 ml), and treated with hydroxylamine hydrochloride (7.65 g, 110 mmoles), then with 25% sodium methoxide (2.2 g, 10 mmoles). After 2 hours at room temperature additional 25% sodium methoxide (21.6 g, 100 mmoles) was added and after 15 minutes the solution was filtered. The filtrate was concentrated in vacuo to a residue, which was dissolved in methylene chloride (150 ml) and filtered. The filtrate was concentrated in vacuo, and the residue was triturated from cold ether, then from cold acetonitrile ether to afford 8.09 g (36%) of fine colorless needles, mp 194°-195° C.

Anal. Calc. for C$_{12}$H$_{21}$N$_3$O: C,64.54; H,9.48; N,18.82. Found: C,64.31; H,9.62; N,18.78.

EXAMPLE I

4-Amino-5-chloro-N-[2-[(dimethylamino)methyl]-1-azabicyclo[2.2.2]oct-3-yl]-2-methoxy-benzamide

A. 2-(Dimethylaminomethyl)-1-azabicyclo[2.2.2]octan-3-one oxime

A solution of 3-quinuclidinone hydrochloride (4.04 g, 25 mmoles) in 2:1 ethanol/water (6 ml) was treated with sodium hydroxide (1.0 g, 25 mmoles) and stirred at 25° C. for 20 minutes. Aqueous formaldehyde (37%, 2.8 ml) and aqueous dimethylamine (40%, 4.8 ml) were added, and the mixture was refluxed for 1.5 hours, cooled, and concentrated in vacuo. The residue was dissolved in methylene chloride, dried (Na$_2$SO$_4$), concentrated in vacuo, dissolved in methanol (30 ml), and treated with hydroxylamine hydrochloride (2.09 g, 30 mmoles), followed by 25% sodium methoxide/methanol (1.08 g, 5 mmoles). After 40 minutes at 25° C. and 20 minutes at 50° C., the mixture was cooled and treated with additional 25% sodium methoxide/methanol (5.41 g, 25 mmoles). The methanol was removed in vacuo and replaced with methylene chloride, and the mixture was filtered to remove inorganic solids. Trituration of the concentrated residue from cold petroleum ether containing a small amount of ether provided 3.77 g (76%) of a white solid.

B.
2-[(Dimethylamino)methyl]-1-azabicyclo[2.2.2]octan-3-amine

A solution of 2-(dimethylaminomethyl)-1-azabicyclo[2.2.2]octan-3-one oxime (3.55 g, 18 mmoles) in reagent grade ethanol (150 ml) was treated with Raney Nickel and hydrogenated in a Parr apparatus at room temperature and 55–58 psi for 18 hours. The product solution was filtered through Celite ®, concentrated in vacuo, and subjected to bulb-to-bulb distillation (bp 100°–120° C. at 0.30 mm Hg) to provide 2.57 g (78%) of a colorless oil. The product was shown to be a mixture of cis:trans (1:3) isomers by nmr and glc analysis.

C.
4-Amino-5-chloro-N-[2-[(dimethylamino)methyl]-1-azabicyclo[2.2.2]oct-3-yl)-2-methoxybenzamide A solution of 4-amino-5-chloro-2-methoxybenzoic acid (2.22 g, 11 mmoles) and triethylamine (1.12 g, 11 mmoles) in anhydrous methylene chloride (35 ml) under nitrogen was cooled (0° C.) and treated dropwise with ethyl chloroformate (1.2 g, 11 mmoles). After 45 minutes at 0° C., the solution was cooled (−55° C.) and treated dropwise with 2-(dimethylaminomethyl)-1-azabicyclo[2.2.2]octan-3-amine (2.11 g, 11.5 mmoles) in 7 ml of methylene chloride. The solution was warmed to 25° C. over one hour, stirred for one hour, and diluted with methylene chloride to a total volume of 100 ml. The organic solution was washed with 1.0N sodium hydroxide (2×35 ml), saturated aqueous sodium bicarbonate (35 ml), and brine (35 ml), dried (Na$_2$SO$_4$), and concentrated in vacuo to provide 2.94 g (73%) of an oil.

D.
4-Amino-5-chloro-N-[2-[(dimethylamino)methyl]-1-azabicyclo[2.2.2]oct-3-yl]-2-methoxybenzamide, hydrobromide (2.5), hydrate, cis:trans (1:3)

A solution of the above prepared benzamide (1.90 g, 5.18 mmoles) in methylene chloride (10 ml) was treated with excess HBr/methylene chloride, and a precipitate immediately formed. The reaction mixture was cooled, filtered under nitrogen, and the salt dried in vacuo in the presence of Drierite ® and solid sodium hydroxide to yield 2.38 g (78%) of a 1:3 mixture of the cis and trans isomers of the 2.5 hydrobromide salt monohydrate as a hygroscopic white solid, no melting point.
Anal. Calc. for C$_{18}$H$_{27}$ClN$_4$O$_2$•2.5 HBr•H$_2$O: C,36.82; H,5.41; N,9.54. Found: C,36.71; H,5.72; N,9.14.

EXAMPLE II

4-Amino-5-chloro-N-[2-[(dimethylamino)methyl]-1-azabicyclo[2.2.2]oct-3-yl]-2-[2-(methylthio)ethoxy]benzamide A.
4-Amino-5-chloro-N-(2-[(dimethylamino)methyl]-1-azabicyclo[2.2.2]oct-3-yl)-2-(2-methylthioethyl)benzamide A suspension of 4-amino-5-chloro-2-[2-(methylthio)ethoxy]benzoic acid in anhydrous tetrahydrofuran (10 ml) was treated with 1,1'-carbonyldiimidazole (1.71 g, 10.5 mmoles), stirred at 25° C. for 90 minutes, then added to a cooled (0° C.) solution of 2-[(dimethylamino)methyl]-1-azabicyclo[2.2.2]octan-3-amine (2.11 g, 11.5 mmoles) in anhydrous tetrahydrofuran (10 ml) under nitrogen. After a period of 24 hours, the solution was concentrated in vacuo and partitioned between methylene chloride (50 ml) and 1.5N sodium hydroxide (20 ml). The organic solution was separated and washed with 1.5N sodium hydroxide (20 ml), saturated aqueous sodium bicarbonate (20 ml), and brine (20 ml), then dried (Na$_2$SO$_4$) and concentrated in vacuo. Filtration through alumina (eluted with 5% methanol/methylene chloride) and trituration from petroleum ether provided 3.45 g (81%) of a colorless foam.

B.
4-Amino-5-chloro-N-[2-[(dimethylamino)methyl]-1-azabicyclo[2.2.2]oct-3-yl]-2-[2-(methylthio)ethoxy]benzamide, hydrobromide (2.5), monohydrate, cis:trans (1:3)

A solution of the benzamide prepared above (1.72 g, 4.03 mmoles) in methylene chloride (10 ml) was treated with excess hydrogen bromide/methylene chloride and filtered under nitrogen. The solid was collected and dried in vacuo to yield 2.0 g (77%) of a 1:3 mixture of cis and trans isomers of the title compound as a 2.5 hydrobromide monohydrate salt as a hygroscopic white solid, no melting point.
Anal. Calc. for C$_{20}$H$_{31}$ClN$_4$O$_2$S•2.5HBr•H$_2$O: C,37.11; H,5.53; N,8.65. Found: C,37.42; H,5.24; N,8.43.

EXAMPLE III

5-Chloro-N-[2-[(dimethylamino)methyl]-1-azabicyclo[2.2.2]oct-3-yl]-2-methoxy-4-(methylamino)benzamide A.
5-Chloro-N-(2-[(dimethylamino)methyl]-1-azabicyclo[2.2.2]oct-3-yl)-2-methoxy-(4-methylamino)benzamide A suspension of 5-chloro-2-methoxy-4-(methylamino)benzoic acid (2.02 g, 10 mmoles) in anhydrous tetrahydrofuran (10 ml) was treated with 1,1'-carbonyldiimidazole (1.71 g, 10.5 mmoles), maintained at room temperature for 90 minutes, then added to a cooled (0° C.) solution of 2-[(dimethylamino)methyl]-1-azabicyclo[2.2.2]octan-3-amine (2.11 g, 11.5 mmoles) in anhydrous tetrahydrofuran (10 ml) under nitrogen. After 24 hours at 25° C., the solution was concentrated in vacuo and partitioned between methylene chloride (50 ml) and 1.5N sodium hydroxide (20 ml). The organic solution was separated and washed with 1.5N sodium hydroxide (20 ml), saturated aqueous sodium bicarbonate (20 ml), brine (20 ml), and concentrated in vacuo. Filtration through alumina (eluted with 5% methanol/methylene chloride) provided 3.55 g (93%) of a colorless foam.

B.
5-Chloro-N-[2-[(dimethylamino)methyl]-1-azabicyclo[2.2.2]oct-3-yl)-2-methoxy-4-methylamino)benzamide, hydrobromide (2.5), hydrate A solution of the benzamide prepared above (3.30 g, 8.66 mmoles) in anhydrous methylene chloride (15 ml) was treated with excess HBr/methylene chloride and the precipitate was filtered under nitrogen, collected, and dried in vacuo to provide 3.94 g (77%) of a 1:3 mixture of cis and trans isomers of the title compound as the 2.5 hydrobromide salt, monohydrate, as a hygroscopic white solid, no melting point.

Anal. Calc. for $C_{19}H_{29}ClN_4O_2 \cdot 2.5HBr \cdot 0.5H_2O$: C,38.54; H,5.53; N,9.46. Found: C,38.56; H,5.37; N,9.01.

EXAMPLE IV

4-Amino-5-chloro-2-methoxy-N-[2-(1-piperidinylmethyl)-1-azabicyclo[2.2.2]oct-3-yl]benzamide

A.

2-(1-Piperidinemethyl)-1-azabicyclo[2.2.2]octan-3-amine

A suspension of 2-(1-piperidylmethyl)-1-azabicyclo[2.2.2]octan-3-one oxime (5.46 g, 23 mmoles) in methanol (150 ml) was treated with Raney Nickel and hydrogenated in a Parr apparatus for 16 hours at 55–60 psi and room temperature. The solution was filtered through Celite ® and concentrated in vacuo to provide 4.55 g (89%) of a viscous colorless oil (rapidly carbonates). This product was shown by nmr and glc analysis to be a 2:3 mixture of cis:trans isomers.

B.

4-Amino-5-chloro-2-methoxy-N-[2-(1-piperidinylmethyl)-1-azabicyclo[2.2.2]oct-3-yl]benzamide cis:trans (2:3)

A suspension of 4-amino-5-chloro-2-methoxybenzoic acid (1.82 g, 9.0 mmoles) in anhydrous tetrahydrofuran (10 ml) was treated with 1,1'-carbonyldiimidazole (1.49 g, 9.2 mmoles), stirred at room temperature for 90 minutes, then added to a cooled (0° C.) solution of the amine prepared above (2.12 g, 9.5 mmoles) in anhydrous tetrahydrofuran (10 ml) under nitrogen. After 18 hours at room temperature the solution was concentrated in vacuo and partitioned between methylene chloride (100 ml) and 1.0N sodium hydroxide (40 ml). The organic solution was separated and washed with 1.0N sodium hydroxide (40 ml), saturated aqueous sodium bicarbonate (40 ml), and brine (40 ml), dried ($Na_2SO_4$), and concentrated in vacuo. Filtration through alumina (eluted with 10% methanol/ethyl acetate), trituration from cold ether, and recrystallization from acetonitrile yielded 2.24 g (61%) of a 2:3 mixture of cis and trans isomers as pale tan crystals, mp 185°–187° C.

Anal. Calc. for $C_{21}H_{31}ClN_4O_2$: C,61.98; H,7.68; N,13.77. Found: C,61.59; H,7.70; N,13.91.

EXAMPLE V

5-Chloro-2-methoxy-4-(methylamino)-N-[2-(1-piperidinylmethyl)-1-azabicyclo[2.2.2]oct-3-yl]benzamide

A.

5-Chloro-2-methoxy-4-(methylamino)-N-[2-(1-piperidinyl-methyl)-1-azabicyclo[2.2.2]oct-3-yl]benzamide, cis:trans (2:3)

A solution of 5-chloro-2-methoxy-4-(methylamino)-benzoic acid (1.95 g, 9.0 mmoles) in anhydrous tetrahydrofuran (10 ml) was treated with 1,1'-carbonyldiimidazole (1.49 g, 9.2 mmoles), stirred at room temperature for 90 minutes, then added to a cooled (0° C.) solution of 2-(1-piperidylmethyl)-1-azabicyclo[2.2.2]octan-3-amine (2.12 g, 9.5 mmoles) in anhydrous tetrahydrofuran (10 ml) under nitrogen. After 18 hours at room temperature the solution was concentrated in vacuo and partitioned between methylene chloride (100 ml) and 1.0N sodium hydroxide (40 ml). The organic solution was separated and washed with 1.0N sodium hydroxide (40 ml), saturated aqueous sodium bicarbonate (40 ml), and brine (40 ml), dried ($Na_2SO_4$), and concentrated in vacuo. Filtration through alumina (eluted with 15% methanol/ethyl acetate) provided 3.24 g (86%) of a colorless foam.

B.

5-Chloro-2-methoxy-4-(methylamino)-N-[2-(1-piperidinylmethyl)-1-azabicyclo-[2.2.2]oct-3-yl]benzamide cis:trans (2:3), 2.5 hydrobromide, monohydrate A solution of the benzamide prepared above (3.00 g, 7.13 mmoles) in methylene chloride (15 ml) was treated with excess HBr/methylene chloride, and the resultant solid was filtered under nitrogen, washed with methylene chloride, and dried in vacuo. A 4.20 g (92%) quantity of a 2:3 mixture of cis and trans isomers of the title compound 2.5 hydrobromide monohydrate salt as a colorless solid was obtained, and no melting point was observed.

Anal. Calc. for $C_{22}H_{33}ClN_4O_2 \cdot 2.5HBr \cdot H_2O$: C,41.21; H,5.89; N,8.74. Found: C,40.93; H,5.87; N,8.84.

C.

5-Chloro-2-methoxy-4-(methylamino)-N-[2-(1-piperidylmethyl)-1-azabicyclo[2.2.2]oct-3-yl]-benzamide cis:trans (2:3), dihydrochloride, monohydrate A solution of 5-chloro-2-methoxy-4-(methylamino)-N-[2-(1-piperidinylmethyl)-1-azabicyclo[2.2.2]oct-3-yl]benzamide (6.70 g, 15.9 mmoles) in anhydrous tetrahydrofuran (200 ml) was treated with excess ethereal hydrochloric acid, and the resultant precipitate was filtered under nitrogen, washed with tetrahydrofuran, and collected. Drying in vacuo at 82° C. in the presence of potassium hydroxide provided 7.64 g (94%) of the dihydrochloride salt, monohydrate, of the title compound as a mildly hygroscopic colorless solid, and no melting point was observed.

Anal. Calc. for $C_{22}H_{33}ClN_4O_2 \cdot 2HCl \cdot H_2O$: C,51.62; H,7.29; N,10.94. Found: C,51.95; H,7.35; N,10.69.

EXAMPLE VI

4-Amino-5-chloro-2-methoxy-N-[2-(1-pyrrolidinylmethyl)-1-azabicyclo[2.2.2]oct-3-yl]benzamide

A.

2-(1-Pyrrolidinylmethyl)-1-azabicyclo[2.2.2]octan-3-amine

A suspension of 2-(1-pyrrolidinylmethyl)-1-azabicyclo-[2.2.2]octan-3-one oxime (8.94 g, 40 mmoles) in methanol (250 ml) in a Parr bottle was treated with Raney Nickel and subjected to hydrogenation over 16 hours at 50–60 psi pressure. The resultant solution was filtered through Celite ® under nitrogen, and concentrated in vacuo to provide 7.30 g (87%) of a colorless oil.

B.

4-Amino-5-chloro-2-methoxy-N-[2-(1-pyrrolidinylmethyl)-1-azabicyclo[2.2.2]oct-3-yl]benzamide, cis:trans (2:3)

A suspension of 4-amino-5-chloro-2-methoxybenzoic acid (2.93 g, 14.5 mmoles) in anhydrous tetrahydrofuran (20 ml) under nitrogen was treated with 1,1'-carbonyldiimidazole (2.44 g, 15 mmoles), stirred for 90 minutes, cooled (0° C.), and treated with the amine prepared above (3.14 g, 15 mmoles), in anhydrous tetrahydrofuran (10 ml). After 24 hours at room temperature and one hour at 60° C., the solution was concentrated in vacuo and partitioned between methylene chloride (100 ml) and 1.0N aqueous sodium carbonate (50 ml). The organic layer was separated and the aqueous solution was extracted with methylene chloride (30 ml). The combined organic solution was washed with brine (50 ml), dried (Na₂SO₄), and filtered through alumina (eluted with 5% methanol/methylene chloride). The filtrate was concentrated in vacuo and triturated successively from ether and acetonitrile to provide 3.25 g (57%) of a colorless solid.

C.
4-Amino-5-chloro-2-methoxy-N-[2-(1-pyrrolidinylmethyl)-1-azabicyclo[2.2.2]oct-3-ylbenzamide dihydrochloride hemihydrate A suspension of the benzamide prepared above (1.55 g, 3.94 mmoles) in anhydrous tetrahydrofuran (50 ml) was diluted with methanol to promote solubility, then treated with excess HCl/ether. The suspension was filtered under nitrogen, and the solid was triturated from acetonitrile to yield 1.30 g (69%) of the dihydrochloride hemihydrate salt of the title compound as a colorless hygroscopic solid, mp 183°-185° C. (dec).

Anal. Calc. for C₂₀H₂₉ClN₄O₂•2HCl•0.5H₂O: C,50.59; H,6.79; N,11.80. Found: C,50.54; H,6.80; N,11.78.

EXAMPLE VII
5-Chloro-2-methoxy-4-(methylamino)-N-[2-(1-pyrrolidinylmethyl)-1-azabicyclo[2.2.2]oct-3-yl]benzamide

A.
5-Chloro-2-methoxy-4-(methylamino)-N-[2-(1-pyrrolidinyl-methyl)-1-azabicyclo[2.2.2]oct-3-yl]benzamide, cis:trans (2:3)

a suspension of 5-chloro-2-methoxy-4-(methylamino)benzoic acid (3.13 g, 14.5 mmoles) in anhydrous tetrahydrofuran (20 ml) under nitrogen was treated with 1,1'-carbonyldiimidazole (2.44 g, 15 mmoles), stirred for 90 minutes, cooled (0° C.), and treated with 2-(1-pyrrolidinylmethyl)-1-azabicyclo[2.2.2]octane-3-amine (3.14 g, 15.0 mmoles) in anhydrous tetrahydrofuran (10 ml). After 24 hours at room temperature and one hour at 60° C., the solution was concentrated in vacuo and partitioned between methylene chloride (100 ml) and 1.0N aqueous sodium carbonate (50 ml). The organic layer was separated and the aqueous solution was extracted with methylene chloride (40 ml). The combined organic solution was washed with brine (50 ml), dried (Na₂SO₄), concentrated in vacuo, dissolved in tetrahydrofuran, and filtered. The filtrate was passed through alumina (eluted with 15% methanol/ethyl acetate), and concentrated in vacuo to provide 3.71 g (63%) of a colorless foam.

B.
5-Chloro-2-methoxy-4-(methylamino)-N-[2-(1-pyrrolidinylmethyl)-1-azabicyclo[2.2.2]oct-3-yl]benzamide, cis:trans (2:3), dihydrochloride, monohydrate A solution of the benzamide prepared above (3.71 g, 9.12 mmoles) in anhydrous tetrahydrofuran (75 ml) was treated with excess ethereal hydrogen chloride and filtered under nitrogen. The solid was collected and triturated from cold acetonitrile to yield 2.67 g (59%) of the hemihydrate of the dihydrochloride salt as a colorless hygroscopic solid, mp 172°-174° C. (dec).

Anal. Calc. for C₂₁H₃₁ClN₄O₂•2HCl•H₂O: C,50.66; H,7.09; N,11.25. Found: C,50.33; H,7.25; N,11.41.

EXAMPLE VIII
5-Chloro-2-methoxy-4-(methylamino)-N-[2-(4-morpholinylmethyl)-1-azabicyclo-[2.2.2]oct-3-yl]benzamide

A.
2-(4-Morpholinomethyl)-1-azabicyclo[2.2.2]octan-3-one oxime

A solution/suspension of 3-quinuclidinone hydrochloride (16.2 g, 0.1 mole) in ethanol (25 ml) and water (5 ml) was treated with 50% sodium hydroxide (9.0 g, 0.11 mole) and stirred at room temperature for 30 minutes. Separately a cooled (0° C.) solution of morpholine (17.5 ml, 0.2 mole) in ethanol (25 ml) was treated with 37% aqueous formaldehyde (15.4 ml, 0.2 mole), and the mixture was stirred at room temperature for 10 minutes. The two solutions were combined and refluxed for one hour, then cooled and added to ether (350 ml). Magnesium sulfate was added and the mixture was filtered, concentrated in vacuo, the residue dissolved in methanol (50 ml), and added to a cooled (0° C.) suspension of hydroxylamine hydrochloride (8.4 g, 0.12 mole), which had been treated with 25% sodium methoxide/methanol (26.0 g, 0.12 mole). After one hour at 25° C., additional hydroxylamine hydrochloride (5.6 g, 0.08 mole) was added, followed by 25% sodium methoxide (17.3 g, 0.08 mole). After one hour at room temperature and two hours at 60° C., the mixture was filtered and concentrated in vacuo. The residue was dissolved in methylene chloride and filtered, and the filtrate was concentrated in vacuo and triturated from cold ether to provide 14.3 g of a pale tan solid. Recrystallization from acetonitrile containing a little methanol afforded 9.68 g (40%) of a colorless solid, mp 204°-205° C. (dec).

B.
2-(4-Morpholinomethyl)-1-azabicyclo[2.2.2]octan-3-amine, cis:trans (1:1)

A suspension/solution of the oxime prepared above (4.00 g, 16.7 mmoles) in methanol (200 ml) in a Parr bottle was treated with Raney Nickel, and subjected to hydrogenation over 18 hours at 50–60 psi pressure. The product solution was filtered through Celite® and concentrated in vacuo, and the residue was dissolved in tetrahydrofuran, filtered through Celite, and concentrated to provide 3.57 g (95%) of a colorless oil.

C.
5-Chloro-2-methoxy-4-(methylamino)-N-[2-(4-morpholinomethyl)-1-azabicyclo[2.2.2]oct-3-yl]benzamide, cis:trans (1:1)

A solution/suspension of 5-chloro-2-methoxy-4-(methylamino)benzoic acid (3.24 g, 15.0 mmoles) in anhydrous tetrahydrofuran (20 ml) under nitrogen was treated with 1,1'-carbonyldiimidazole (2.51 g, 15.5 mmoles) and stirred for one hour, then the resultant thick suspension was degassed by passage of a stream of nitrogen for 30 minutes. A solution of the amine prepared above (3.61 g, 16 mmoles) in anhydrous tetrahydrofuran (10 ml) was added to the cooled (0° C.) solution, and the mixture was stirred for 18 hours at room temperature, and for one hour at 60° C., then concentrated in vacuo. The residue was partitioned between methylene chloride (150 ml) and 1.0N sodium carbonate (50 ml), and the organic layer was separated. The aqueous solution was extracted with methylene chloride (50 ml), and the combined organic solution was washed with brine (100 ml), dried (Na₂SO₄), passed through a short column of alumina (eluted with 2% methanol/methylene chloride), and concentrated in vacuo to provide 5.37 g (85%) of a colorless foam.

D.

5-Chloro-2-methoxy-4-(methylamino)-N-[2-(4-morpholinylmethyl)-1-azabicyclo[2.2.2]oct-3-yl]benzamide, cis:trans (1:1), dihydrochloride, hemihydrate A solution of the benzamide prepared above (5.29 g, 12.5 mmoles) in tetrahydrofuran (100 ml) was treated with excess ethereal hydrogen chloride, filtered under nitrogen, and the solid was collected and dried in vacuo at 80° C. in the presence of potassium hydroxide to yield 5.43 g (86%) of the hemihydrate of the dihydrochloride salt of the title compound as a colorless hygroscopic solid, and no melting point was observed.

Anal. Calc. for $C_{21}H_{31}ClN_4O_2 \cdot 2HCl \cdot 0.5H_2O$: C,49.96; H,6.79; N,11.10. Found: C,49.93; H,6.90; N,10.89.

EXAMPLE IX

4-Amino-5-chloro-N-[2-(di-n-propylaminomethyl)-1-azabicyclo[2.2.2]oct-3-yl]-2-methoxybenzamide

A.

2-(Di-n-propylaminomethyl)-1-azabicyclo[2.2.2]octan-3-one oxime

A solution/suspension of quinuclidin-3-one hydrochloride (32.33 g, 0.2 mole) in ethanol (13 ml) and water (13 ml) was treated with 50% sodium hydroxide (17 g, 0.21 mole) and stirred for 30 minutes. Separately, a cooled (0° C.) solution of di-n-propylamine (56 ml, 0.40 mole) in ethanol (20 ml) was treated dropwise with 37% aqueous formaldehyde (31 ml, 0.4 mole) and stirred for 10 minutes. The two solutions were combined, refluxed for 2 hours, then added to ether (250 ml). The organic layer was separated and the aqueous solution was extracted with ether. The organic solution was dried (MgSO$_4$), concentrated in vacuo, dissolved in methanol (200 ml), and cooled (0° C.). Hydroxylamine hydrochloride (27.8 g, 0.4 mole) was added, and this was followed with 25% sodium methoxide/methanol (86.5 g, 0.4 mole). After 3 hours at room temperature, the solution was filtered, concentrated in vacuo, dissolved in ether, and filtered. The filtrate was concentrated in vacuo and passed through a short column of alumina (eluted with 3% methanol/methylene chloride). The concentrated filtrate was triturated from petroleum ether to provide 19.2 g (38%) of a pale yellow solid.

B.

2-(Di-n-propylaminomethyl)-1-azabicyclo[2.2.2]octan-3-amine, cis:trans(1:2)

A solution of the oxime prepared above (5.07 g, 20 mmoles) in methanol (200 ml) in a Parr bottle was treated with Raney Nickel, and subjected to hydrogenation over 6 hours at 50–60 psi pressure. The product solution was filtered through Celite ®, and concentrated in vacuo to provide 4.40 g (92%) of a pale yellow oil.

C.

4-Amino-5-chloro-N-[2-(di-n-propylaminomethyl)-1-azabicyclo[2.2.2]-oct-3-yl]-2-methoxybenzamide, cis:trans (1:2)

A solution of 4-amino-5-chloro-2-methoxybenzoic acid (2.73 g, 13.5 mmoles) in anhydrous tetrahydrofuran (15 ml) under nitrogen was treated with 1,1'-carbonyldiimidazole (2.24 g, 13.8 mmoles) and stirred at 25° C. for one hour. A stream of nitrogen was passed through the solution for 20 minutes, and a solution of the amine prepared above (3.47 g, 14.5 mmoles) in tetrahydrofuran (10 ml) was added dropwise. The mixture was maintained at room temperature for 18 hours, and at 50° C. for one hour, then concentrated in vacuo. The residue was partitioned between methylene chloride (150 ml) and 1.0N aqueous sodium carbonate (100 ml), and the organic layer was separated. The aqueous solution was extracted with methylene chloride (75 ml), and the combined organic solution was dried (Na$_2$SO$_4$) and concentrated in vacuo. Alumina filtration (eluted with 3% methanol/methylene chloride) provided 4.59 g (80%) of a colorless foam.

D.

4-Amino-5-chloro-N-[2-(di-n-propylaminomethyl)-1-azabicyclo[2.2.2]oct-3-yl]-2-methoxybenzamide, cis:trans (1:2), dihydrochloride, monohydrate A solution of the benzamide (2.90 g, 6.86 mmoles) in anhydrous tetrahydrofuran (100 ml) was treated with excess ethereal hydrogen chloride and filtered under nitrogen. The resultant solid was dried in vacuo overnight at 80° C. in the presence of solid potassium hydroxide to yield 3.10 g (88%) of the dihydrochloride monohydrate salt of the title compound as a colorless hygroscopic solid, and no melting point was observed.

Anal. Calc. for $C_{22}H_{35}ClN_4O_2 \cdot 2 HCl \cdot H_2O$: C,51.42; H,7.65; N,10.90. Found: C,51.58; H,7.81; N,10.92.

EXAMPLE X

5-Chloro-N-[2-(di-n-propylaminomethyl)-1-azabicyclo[2.2.2]oct-3-yl]-2-methoxy-4-(methylamino)benzamide

A.

5-Chloro-N-[2-(di-n-propylaminomethyl)-1-azabicyclo[2.2.2]oct-3-yl]-2-methoxy-4-(methylamino)benzamide A solution of 5-chloro-2-methoxy-4-(methylamino)-benzoic acid (3.35 g, 15.5 mmoles) in anhydrous tetrahydrofuran (20 ml) under nitrogen was treated with 1,1'-carbonyldiimidazole (2.56 g, 15.8 mmoles), and stirred for one hour at room temperature. Nitrogen was bubbled through the solution for 20 minutes, and a solution of 2-(di-n-propylaminomethyl)-1-azabicyclo[2.2.2]-octan-3-amine (3.95 g, 15.8 mmoles) in tetrahydrofuran (10 ml) was added dropwise. The mixture was maintained at room temperature for 18 hours, and at 50° C. for 1 hour, then concentrated in vacuo. The residue was partitioned between methylene chloride and 1.0N aqueous sodium carbonate, and the organic layer was separated. The aqueous solution was extracted with methylene chloride, and the combined organic solution was dried (Na$_2$SO$_4$) and concentrated in vacuo. The residue was filtered through alumina (eluted with 3% methanol/methylene chloride) to provide 5.38 g (79%) of a colorless foam.

B.

5-Chloro-N-[2-(di-n-propylaminomethyl)-1-azabicyclo[2.2.2]oct-3-yl]-2-methoxy-4-(methylamino)benzamide, cis:trans (1:2), dihydrochloride, hemihydrate A solution of the benzamide prepared above (3.10 g, 7.09 mmoles) in tetrahydrofuran (30 ml) was treated with excess ethereal hydrogen chloride, filtered and collected under nitrogen, and dried in vacuo to yield 3.05 g (83%) of the hemihydrate of the dihydrochloride salt of the title compound as a hygroscopic voluminous white solid, mp 165°–168° C.

Anal. Calc. for $C_{23}H_{37}ClN_4O_2 \cdot 2$ HCl$\cdot 0.5$ $H_2O$: C,53.23; H,7.77; N,10.80. Found: C,53.08; H,7.88; N,10.71.

EXAMPLE XI

4-Amino-5-chloro-2-methoxy-N-[2-(4-morpholinylmethyl)-1-azabicyclo[2.2.2]oct-3-yl]benzamide

A.

4-Amino-5-chloro-2-methoxy-N-[2-(4-morpholinylmethyl)-1-azabicyclo[2.2.2]oct-3-yl]benzimide, cis:trans (1:1)

A solution of 4-amino-5-chloro-2-methoxybenzoic acid (1.61 g, 8.0 mmoles) in anhydrous tetrahydrofuran (10 ml) under nitrogen was treated with 1,1'-carbonyldiimidazole (1.33 g, 8.2 mmoles), stirred for one hour at room temperature, and degassed with a stream of nitrogen over 20 minutes. A solution of 2-(4-morpholinomethyl)-1-azabicyclo[2.2.2]octan-3-amine, cis:trans (1:1) (1.94 g, 8.6 mmoles) in anhydrous tetrahydrofuran (10 ml) was added to the cooled (0° C.) solution dropwise, and the mixture was stirred for 18 hours at room temperature and for one hour at 50° C., then concentrated in vacuo. The residue was partitioned between methylene chloride (150 ml) and 1.0N sodium carbonate, and the organic layer was separated. The aqueous solution was extracted with methylene chloride, and the organic solution was dried ($Na_2SO_4$) and concentrated in vacuo. The residue was filtered through alumina (eluted with 5% methanol/methylene chloride) to provide 2.42 g (74%) of a colorless foam.

B.

4-Amino-5-chloro-2-methoxy-N-[2-(4-morpholinylmethyl)-1-azabicyclo[2.2.2]oct-3-yl]benzamide, cis:trans (1:1), dihydrochloride, monohydrate A solution of the benzamide above (1.42 g, 3.5 mmoles) in anhydrous tetrahydrofuran (10 ml) was treated with excess ethereal HCl, filtered, and washed with anhydrous tetrahydrofuran. The solid was collected and dried in vacuo at 80° C. to yield 1.27 g (73%) of the monohydrate of the dihydrochloride salt of the title compound as a colorless hygroscopic solid.

Anal. Calc. for $C_{20}H_{29}ClN_4O_2 \cdot 2$ HCl$\cdot H_2O$: C,48.06; H,6.65; N,11.21. Found: C,47.73; H,6.80; N,11.18.

EXAMPLE XII

N-[[2-(Dimethylamino)methyl]-1-azabicyclo[2.2.2]oct-3-yl]-1H-indazole-3-carboxamide A suspension of 1H-indazole-3-carboxylic acid (2.06 g, 0.0127 mole) in anhydrous tetrahydrofuran (10 ml) under nitrogen is treated with 1,1'-carbonyldiimidazole (1.54 g, 0.0095 mole) and after ten minutes is diluted with N,N-dimethylformamide (4 ml). The mixture is stirred for one hour and degassed under a stream of nitrogen for 15 minutes. To this solution is added dropwise a solution of the 2-[(dimethylamino)methyl]-1-azabicyclo[2.2.2]octan-3-amine (2.57 g, 0.014 mole) intermediate of Example I in tetrahydrofuran/dimethylformamide (5 ml each). After stirring for 18 hours at ambient temperature and 4 hours at 50°, the mixture is concentrated in vacuo and the residue is partitioned between methylene chloride (50 ml) and 1.5N sodium hydroxide solution (20 ml). The methylene chloride layer is separated, washed with water (20 ml), dried over magnesium sulfate, and concentrated in vacuo to provide the title compound.

EXAMPLE XIII 2-(1-Piperidinylmethyl)-1-azabicyclo[2.2.2]oct-3-yl 1-methyl-1H-indole-3-carboxylate

I. 2-(1-Piperidinylmethyl)-1-azabicyclo[2.2.2]octan-3-ol trans isomer

A.

2-(1-Piperidinylmethyl)-1-azabicyclo[2.2.2]octan-3-one

A reaction flask containing 2-methylenequinuclidin-3-one (6.86 g, 50 mmoles) and a magnetic stir bar was charged with piperidine (12 ml, 120 mmoles). The mixture was stirred at room temperature for 18 hours, and the mixture was added to hexane (300 ml). The solution was filtered through Celite ® and the filtrate was concentrated in vacuo (maximum temperature 60° C.) to provide 11.03 g (99%) of the product as a pale yellow solid, mp 34°–37° C.

B.

2-(1-Piperidinylmethyl)-1-azabicyclo[2.2.2]octan-3-ol trans isomer

A solution of 2-(1-piperidinylmethyl)-1-azabicyclo[2.2.2]octan-3-one (8.90 g, 40 mmoles) in absolute ethanol (40 ml) was treated dropwise with a solution of sodium borohydride (1.15 g, 30.4 mmoles) in absolute ethanol (40 ml). The solution was stirred at room temperature for 18 hours, concentrated in vacuo, and diluted with water (100 ml). The aqueous solution was treated with potassium carbonate and extracted with ether, and the combined organic extracts were dried ($MgSO_4$) and concentrated in vacuo. The residual solid was recrystallized from acetonitrile to afford 3.32 g (37%) of the trans isomer as colorless crystals, mp 130°–131° C.

II. 2-(1-Piperidinylmethyl)-1-azabicyclo[2.2.2]octan-3-ol cis isomer

A solution of 2-(1-piperidinylmethyl)-1-azabicyclo[2.2.2]octan-3-one (8.90 g, 40 mmoles) in absolute ethanol (40 ml) was treated dropwise with a solution of sodium borohydride (1.15 g, 30.4 mmoles) in absolute ethanol (40 ml). The solution was stirred at room temperature for 18 hours, concentrated in vacuo, and diluted with water (100 ml). The aqueous solution was treated with potassium carbonate and extracted with ether, and the combined organic extracts were dried ($MgSO_4$) and concentrated in vacuo. The residual solid was recrystallized from acetonitrile to afford 3.32 g (37%) of the trans isomer as colorless crystals, mp 130°–131° C.

The mother liquors were concentrated in vacuo and passed through a short column of alumina (eluted with 10% methanol/tetrahydrofuran). The filtrate was concentrated in vacuo and the residue was recrystallized from cold (−30° C.) acetonitrile to afford 4.15 g (46%) of the cis isomer as colorless crystals, mp 60.0°–62.5° C.

III. 2-(1-Piperidinylmethyl)-1-azabicyclo[2.2.2]oct-3-yl 1-methyl-1H-indole-3-carboxylate trans isomer A cooled (0° C.) solution of trans-2-(1-piperidinylmethyl)-1-azabicyclo[2.2.2]octan-3-ol (1.70 g, 8.0 mmoles) in anhydrous tetrahydrofuran (10 ml) under nitrogen was treated with 2.45N n-butyllithium/hexane (8.0 mmoles), then stirred for 30 minutes at room temperature and concentrated in vacuo to remove hexane. The residual solid (under nitrogen) was dissolved in anhydrous tetrahydrofuran (12 ml) and treated with 3-(1H-imidazol-1-ylcarbonyl)-1-methyl-1H-indole (1.69 g, 7.5 mmoles), then stirred at room temperature for 18 hours, at 55° C. for two hours, and concentrated in vacuo. The residue was partitioned between 1.0N sodium bicarbonate (50 ml) and toluene (100 ml) containing 2-propanol, and the organic layer was separated. The aqueous solution was extracted with toluene containing 2-propanol, and the combined organic solution was dried ($Na_2SO_4$) and concentrated in vacuo. The residue was filtered through alumina (eluted with 5% methanol/tetrahydrofuran), and the filtrate was concentrated in vacuo and triturated from ether/petroleum ethers (30°–60°). Recrystallization from acetonitrile afforded 2.37 g (83%) of the trans isomer as colorless crystals, mp 143°–144° C.

Anal. Calc. for $C_{23}H_{31}N_3O_2$: C,72.41; H,8.19; N,11.01. Found: C,72.54; H,8.41; N,11.09.

IV. 2-(1-Piperidinylmethyl)-1-azabicyclo[2.2.2]oct-3-yl 1-methyl-1H-indole-3-carboxylate cis isomer Following the procedures above for the trans isomer, cis-2-(1-piperidinylmethyl)-1-azabicyclo[2.2.2]octanol-3-ol (1.79 g, 8.0 mmoles) was treated with n-butyllithium, and then reacted with 3-(1H-imidazol-1-ylcarbonyl)-1-methyl-1H-indole.

Recrystallization from hexane provided 2.08 g (73%) of the cis isomer as colorless crystals, mp 108°–110.5° C.

Anal. Calc. for $C_{23}H_{31}N_3O_2$: C,72.41; H,8.19; N,11.01. Found: C,72.43; H,8.25; N,11.05.

EXAMPLE XIV

2-(1-Piperidinylmethyl)-1-azabicyclo[2.2.2]oct-3-yl 5-chloro-2-methoxy-4-(methylamino)benzoate

I. Trans isomer

A cooled (0° C.) solution of 2-(1-piperidinylmethyl)-1-azabicyclo[2.2.2]octan-3-ol trans isomer (2.47 g, 11 mmoles) in anhydrous tetrahydrofuran (12 ml) under nitrogen was treated with 2.45N n-butyllithium/hexane (11 mmoles), then stirred for 30 minutes at room temperature and concentrated in vacuo to remove the hexane. The residual solid (under nitrogen) was dissolved in anhydrous tetrahydrofuran (15 ml) and treated with 1-[5-chloro-2-methoxy-(4-methylamino)benzoyl]-1H-imidazole (2.66 g, 10 mmoles), then stirred at room temperature for 18 hours, at 60° C. for three hours, and concentrated in vacuo. The residue was partitioned between 1.0 N sodium carbonate (50 ml) and toluene (100 ml) containing 2-propanol, and the organic layer was separated. The aqueous solution was extracted with toluene containing 2-propanol and the combined organic solution was dried ($Na_2SO_4$) and concentrated in vacuo. The residue was filtered through alumina (diluted with 5% methanol/tetrahydrofuran) and the concentrated filtrate was triturated from petroleum ethers (30°–60°) and recrystallized from hexane to afford 3.33 g (79%) of the title trans isomer as a colorless solid, mp 123°–125° C.

Anal. Calc. for $C_{22}H_{32}ClN_3O_3$: C,62.62; H,7.64; N,9.96.

Found: C,62.57; H,7.96; N,9.95.

II. Cis isomer 2-(1-Piperidinylmethyl)-1-azabicyclo[2.2.2]octan-3-ol cis isomer (2.47 g, 11 mmoles) was treated with n-butyllithium/hexane, and then with 1-[5-chloro-2-methoxy-4-(methylamino)benzoyl]-1H-imidazole, following the procedures described above for the corresponding trans isomer.

Recrystallization of the recovered crude product from ethyl acetate/hexane provided 2.57 g (61%) of the title cis isomer as a colorless solid, mp 143°–145° C.

Anal. Calc. for $C_{22}H_{32}ClN_3O_3$: C,62.62; H,7.64; N,9.96.

Found: C,62.53; H,7.92; N,9.93.

Biological Activity

A. Effect Of Invention Compounds On Cisplatin-induced Emesis In Dogs

The procedure used to test compounds of the present invention for antiemetic properties is a modification of the method of Gylys et al, Res. Commun. Chem. Pathol. Pharm., 23, 61(1979).

Adult, mongrel, unfasted dogs of both sexes were randomly assigned into treatment groups, with each treatment group consisting of four dogs. On the dosing day all dogs were given cisplatin, 3.0 mg/kg, intravenously. Sixty minutes later, the dogs in the control treatment group were given deionized water, 0.1 ml/kg intravenously. The dogs in the test group were given a test compound at an appropriate dose intravenously. All doses were administered as a solution by means of a syringe and needle, and each dog's emetic episodes were recorded for 5 hours after the administration of cisplatin.

TABLE A

Antiemetic (dog) at 1.0 mg/kg IV; % inhibition of cisplatin*-induced emesis

| Example Compound | % Inhibition |
| --- | --- |
| I | 96 |
| II | 47 |
| III | 73 |
| IV | 94 |
| V | 99 |
| VI | 87 |
| VII | 87 |
| XI | 21 |
| XIII (cis isomer) | 34 |

*cis-diammine-dichloro-platinum.

B. Effect Of Invention Compounds On Gastric Emptying Of a Test Meal In Fasted Rats The procedure used to test compounds of the present invention for gastric motility enhancing activity was that of Droppleman et al, J. Pharmacol. Methods, 4, 227(1980).

Each animal was dosed intraperitoneally (9.0 mg/kg) with a test compound or control. After 30 minutes each animal was given 3 ml of a methylcellulose-based test meal formulation. Sixty minutes after administration of the test meal, each animal was killed by cervical dislocation, and the stomach was removed and weighed. The stomach was cut open, rinsed and dried, and reweighed. The difference between the full and empty weights (amount of meal remaining in stomach) was subtracted from the original test meal weight to determine the meal amount emptied from the stomach during the test period.

TABLE B

| Gastric emptying (rat) at 9.0 mg/kg IP; % change in meal emptied | |
|---|---|
| Example Compound | % Change |
| I | +36 |
| VI | +33 |

C. Evaluation Of The Example V Invention Compound For Anxiolytic Activity In Mice In A Two-Compartment Light-Dark Apparatus The method has been described by Young and Johnson, Soc. Neurosci. Abs., 1988, 14, 207 and is a modification of the procedures described by Costall and Naylor, Brit. J. Pharmacol. 1988, 93, 985–993; and Crawley, Pharmacol. Biochem. and Behav. 1981, 15, 695–699. A two compartment light-dark activity monitoring device (Digiscan Model RXWZCM16, Omnitech Electronics, Inc., Columbus, Ohio) is used. A 90W light source located 30 cm above the box provides light to the apparatus. Behavioral testing was conducted in a sound attenuated, darkened room illuminated with a red light (25W red bulb) only.

Each animal (mouse) received a dose of either the test, reference, or control article. The mouse was placed at the center of the illuminated area and its behavioral activity tallied over a 5 minute period by use of a Digiscan analyzer. Behavioral variables recorded include: the time spent in the lit and dark areas, the number of rearings in the lit and dark areas, the number of locomotor activity counts in the lit and dark areas, the number of transitions between the lit and dark or dark and lit areas, rearing time in the lit and dark areas, the latency to make the first transition from the lit to the dark areas, locomotor time in the lit and dark areas, and resting time in the lit and dark areas. Appropriate statistical analyses for each measure were performed. Significant increases in one or more of the parameters associated with behavior of the animals in the lit versus the dark areas correspond to active, non-sedating anxiolytic compounds.

TABLE C

| Anxiolytic model (exploratory light/dark test) for the Example V compound | | |
|---|---|---|
| Test Article | Dose mg/kg IP | % Time Spent In Lit Area | Significance $p < 0.05$ |
| Vehicle (Control) | — | 29 | — |
| EXAMPLE V Compound | 10 | 51 | 0.05 |

D. Selective 5-HT antagonist activity

The Example IV compound blocked the contractions of the guinea pig ileum produced by $10^{-6}M$ serotonin with a $pA_2$ value of 6.6.

Based on profiles of similar compounds in standard pharmacological tests, quinuclidine derivatives of the present invention are useful for alleviation of migraine, cluster headache and trigeminal neuralgia symptoms in warm blooded animals.

What is claimed is:

1. A compound corresponding to the formula:

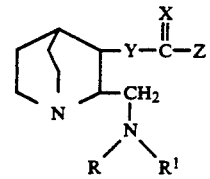

where X is oxygen or sulfur; Y is —NH— or —O—; R and $R^1$ are $C_1$–$C_4$ alkyl, or R and $R^1$ taken together with the connecting nitrogen atom is a 4–6 membered heterocyclic structure selected from azetidine, pyrrolidine, piperidine or morpholine;

Z is

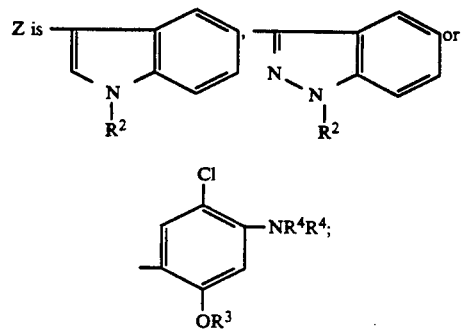

$R^2$ is a hydrogen or a $C_1$–$C_4$ alkyl substituent; $R^3$ is a hydrogen or $C_1$–$C_4$ alkyl, $C_1$–$C_4$ alkenyl, $C_2$–$C_6$ alkylthioalkyl or $C_2$–$C_6$ alkyloxyalkyl substituent; and $R^4$ is hydrogen or a $C_1$–$C_4$ alkyl substituent; the geometrical and optical isomers, or a pharmaceutically acceptable salt thereof.

2. A compound in accordance with claim 1 which is 4-amino-5-chloro-N-[2-[(dimethylamino)methyl]-1-azabicyclo[2.2.2]oct-3-yl]-2-methoxybenzamide.

3. A compound in accordance with claim 1 which is 4-amino-5-chloro-N-[2-[(dimethylamino)methyl]-1-azabicyclo[2.2.2]oct-3-yl]-2-[2-(methylthio)ethoxy]benzamide.

4. A compound in accordance with claim 1 which is 5-chloro-N-(2-[(dimethylamino)methyl]-1-azabicyclo[2.2.2]oct-3-yl]-2-methoxy-4-(methylamino)benzamide.

5. A compound in accordance with claim 1 which is 4-amino-5-chloro-2-methoxy-N-[2-(1-piperidinylmethyl)-1-azabicyclo[2.2.2]oct-3-yl]benzamide.

6. A compound in accordance with claim 1 which is 5-chloro-2-methoxy-4-(methylamino)-N-[2-(1-piperidinylmethyl)-1-azabicyclo[2.2.2]oct-3-yl]benzamide.

7. A compound in accordance with claim 1 which is 5-chloro-2-methoxy-4-(methylamino)-N-[2-(1-pyrrolidinylmethyl)-1-azabicyclo[2.2.2]oct-3-yl]benzamide.

8. A compound in accordance with claim 1 which is 5-chloro-2-methoxy-4-(methylamino)-N-[2-(4-morpholinylmethyl)-1-azabicyclo[2.2.2]oct-3-yl]benzamide.

9. A compound in accordance with claim 1 which is 4-amino-5-chloro-N-[2-[di-n-propylamino)methyl]-1-azabicyclo[2.2.2]-oct-3-yl]-2-methoxybenzamide.

10. A compound in accordance with claim 1 which is 5-chloro-N-[2-[(di-n-propylamino)methyl-1-azabicyclo[2.2.2]oct-3-yl]-2-methoxy-4-(methylamino)benzamide.

11. A compound in accordance with claim 1 which is 4-amino-5-chloro-2-methoxy-N-[2-(4-morpholinylmethyl)-1-azabicyclo[2.2.2]oct-3-yl]benzamide.

12. A compound in accordance with claim 1 which is 4-amino-5-chloro-2-methoxy-N-[2-(1-pyrrolidinylmethyl)-1-azabicyclo[2.2.2]oct-3-yl]benzamide.

13. A compound in accordance with claim 1 which is 2-(1-piperidinylmethyl)-1-azabicyclo[2.2.2]oct-3-yl 1-methyl-1H-indole-3-carboxylate.

14. A compound in accordance with claim 1 which is 2-(1-piperidinylmethyl)-1-azabicyclo[2.2.2]oct-3-yl 5-chloro-2-methoxy-4-(methylamino)benzoate.

15. A compound in accordance with claim 1 which is N-(2-dimethylaminomethyl-1-azabicyclo[2.2.2]oct-3-yl)-1H-indazole-3-carboxamide.

16. A method for the treatment of warm blooded animals for emesis caused by administration of anticancer drugs during cancer treatment which comprises internally administering to said animals an emesis-inhibiting effective amount of a compound corresponding to the formula:

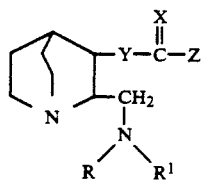

where X is oxygen or sulfur; Y is —NH— or —O—; R and $R^1$ are $C_1$-$C_4$ alkyl, or R and $R^1$ taken together with the connecting nitrogen atom is a 4–6 membered heterocyclic structure selected from azetidine, pyrrolidine, piperidine or morpholine;

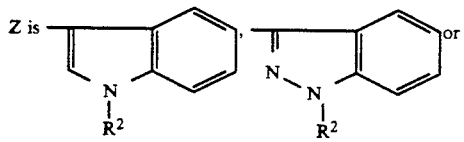

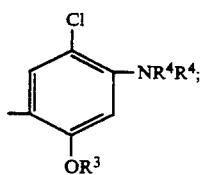

$R^2$ is hydrogen or a $C_1$-$C_4$ alkyl substituent; $R^3$ is a hydrogen or $C_1$-$C_4$ alkyl, $C_1$-$C_4$ alkenyl, $C_2$-$C_6$ alkylthioalkyl or $C_2$-$C_6$ alkyloxyalkyl substituent; and $R^4$ is hydrogen or a $C_1$-$C_4$ alkyl substituent; the geometrical and optical isomers, or a pharmaceutically acceptable salt thereof.

17. A method for the treatment of warm blooded animals for impaired gastrointestinal motility which comprises administering to said animals a gastric motility-enhancing effective amount of a compound corresponding to the formula:

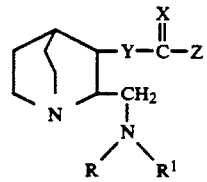

where X is oxygen or sulfur; Y is —NH— or —O—; R and $R^1$ are $C_1$-$C_4$ alkyl, or R and $R^1$ taken together with the connecting nitrogen atom is a 4–6 membered heterocyclic structure selected from azetidine, pyrrolidine, piperidine or morpholine;

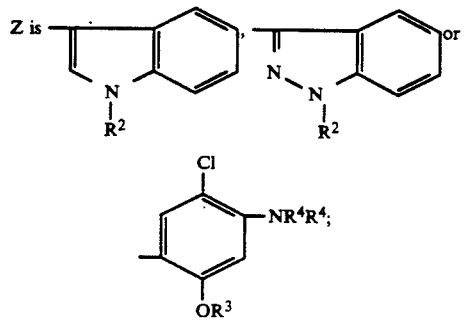

$R^2$ is hydrogen or a $C_1$-$C_4$ alkyl substituent; $R^3$ is a hydrogen or $C_1$-$C_4$ alkyl, $C_1$-$C_4$ alkenyl, $C_2$-$C_6$ alkylthioalkyl or $C_2$-$C_6$ alkyloxyalkyl substituent; and $R^4$ is hydrogen or a $C_1$-$C_4$ alkyl substituent; the geometrical and optical isomers, or a pharmaceutically acceptable salt thereof.

18. A method for the treatment of warm blooded animals for anxiety symptoms which comprises internally administering to said animals an anxiety-alleviating effective amount of a compound corresponding to the formula:

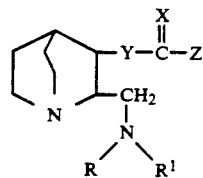

where X is oxygen or sulfur; Y is —NH— or —O—; R and $R^1$ are $C_1$-$C_4$ alkyl, or R and $R^1$ taken together with the connecting nitrogen atom is a 4–6 membered heterocyclic structure selected from azetidine, pyrrolidine, piperidine or morpholine;

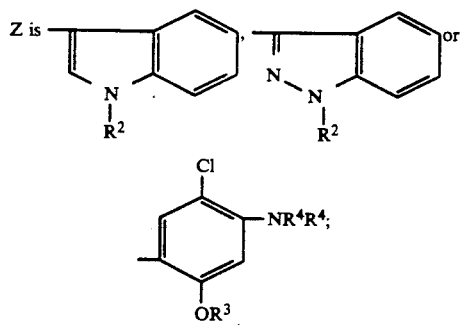

$R^2$ is hydrogen or a $C_1$-$C_4$ alkyl substituent; $R^3$ is a hydrogen or $C_1$-$C_4$ alkyl, $C_1$-$C_4$ alkenyl, $C_2$-$C_6$ alkylthioalkyl or $C_2$-$C_6$ substituent; and $R^4$ is hydrogen or a $C_1$-$C_4$ alkyl substituent; the geometrical and optical isomers, or a pharmaceutically acceptable salt thereof.

* * * * *